(12) United States Patent
Orban, III et al.

(10) Patent No.: US 7,112,172 B2
(45) Date of Patent: Sep. 26, 2006

(54) ENDOSCOPIC ORGAN RETRACTION SYSTEM AND METHOD OF USING THE SAME

(75) Inventors: Joseph P. Orban, III, Norwalk, CT (US); Dean Geraci, Norwalk, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 0 days.

(21) Appl. No.: 10/513,390

(22) PCT Filed: May 19, 2003

(86) PCT No.: PCT/US03/15885

§ 371 (c)(1),
(2), (4) Date: Nov. 1, 2004

(87) PCT Pub. No.: WO03/096907

PCT Pub. Date: Nov. 27, 2003

(65) Prior Publication Data

US 2005/0203344 A1    Sep. 15, 2005

Related U.S. Application Data

(60) Provisional application No. 60/381,721, filed on May 17, 2002.

(51) Int. Cl.
*A61B 1/32*    (2006.01)

(52) U.S. Cl. .................. 600/209; 600/204; 600/206; 600/210

(58) Field of Classification Search .............. 433/37, 433/201, 209, 231; 600/37, 201, 209, 231

See application file for complete search history.

(56) References Cited

U.S. PATENT DOCUMENTS

| | | | |
|---|---|---|---|
| 4,190,042 A | | 2/1980 | Sinnreich |
| 4,654,028 A | | 3/1987 | Suma |
| 4,744,363 A | | 5/1988 | Hasson |
| 4,909,789 A | | 3/1990 | Taguchi et al. |
| 5,178,133 A | | 1/1993 | Pena |
| 5,195,505 A | | 3/1993 | Josefsen |
| 5,242,456 A | | 9/1993 | Nash et al. |
| 5,301,658 A | | 4/1994 | Zhu et al. |
| 5,337,736 A | * | 8/1994 | Reddy ........................ 600/217 |
| 5,339,803 A | * | 8/1994 | Mayzels et al. ............ 600/201 |
| 5,362,294 A | * | 11/1994 | Seitzinger ..................... 600/37 |
| 5,456,695 A | | 10/1995 | Herve Dallemagne |
| 5,486,182 A | * | 1/1996 | Nakao et al. ................ 606/114 |
| RE35,164 E | * | 3/1996 | Kindberg et al. ........... 600/562 |
| 5,520,610 A | * | 5/1996 | Giglio et al. ................ 600/233 |
| 5,656,012 A | * | 8/1997 | Sienkiewicz ................ 600/204 |
| 5,895,352 A | * | 4/1999 | Kleiner ....................... 600/206 |

(Continued)

FOREIGN PATENT DOCUMENTS

EP    0 531 710    3/1993

(Continued)

*Primary Examiner*—Patricia Bianco
*Assistant Examiner*—Patrick J. Kilkenny

(57) ABSTRACT

The present disclosure relates to a retraction system for retracting body organs and/or body tissue in a body cavity. The retraction system includes an elongate shaft configured and dimensioned to be inserted into the body cavity, a retractor device operatively associated with the elongate shaft, the retractor device having a first configuration for insertion into the body cavity and at least a second configuration for retraction of the body organ, and at least one anchor member operatively coupled to the retractor device for anchoring the retractor device to a wall of the body cavity.

6 Claims, 10 Drawing Sheets

U.S. PATENT DOCUMENTS

| | | | |
|---|---|---|---|
| 6,042,536 A * | 3/2000 | Tihon et al. | 600/37 |
| 6,071,235 A * | 6/2000 | Furnish et al. | 600/235 |
| 6,090,041 A * | 7/2000 | Clark et al. | 600/205 |
| 6,258,023 B1 * | 7/2001 | Rogers et al. | 600/37 |
| 6,383,197 B1 * | 5/2002 | Conlon et al. | 606/114 |
| 6,814,700 B1 * | 11/2004 | Mueller et al. | 600/206 |
| 2002/0050277 A1 * | 5/2002 | Beyar | 128/898 |
| 2002/0058856 A1 * | 5/2002 | Peng et al. | 600/37 |
| 2004/0097792 A1 * | 5/2004 | Moll et al. | 600/201 |

FOREIGN PATENT DOCUMENTS

| WO | WO 97/26828 | 7/1997 |
|---|---|---|

* cited by examiner

ENDOSCOPIC ORGAN RETRACTION SYSTEM AND METHOD OF USING THE SAME

CROSS REFERENCE TO RELATED APPLICATIONS

This is a National Stage Application of PCT/US 03/15885 under 35 USC §371(a), which claims priority of U.S. Provisional Patent Application Ser. No. 60/381,721 filed May 17, 2002, the entire contents of which are hereby incorporated by reference.

BACKGROUND

1. Technical Field

The present disclosure relates to devices, systems and methods used for retracting organs and/or body tissue during surgical procedures and, more particularly, to endoscopic or laparoscopic apparatus, systems and methods for retracting or positioning body tissue and/or body organs during minimally invasive surgery.

2. Background of Related Art

As a result of the recent technological improvements in surgical instruments, surgical procedures, using minimally invasive techniques (e.g., endoscopic, laparoscopic, etc.), are routinely performed, which surgical procedures cause less trauma to the patient.

In endoscopic and laparoscopic surgical procedures, it is often necessary to provide instrumentation to move or manipulate tissue and organs located in the area of operation. Generally, laparoscopic surgical procedures involve the introduction of a gas, such as, carbon dioxide, to insufflate a body cavity, e.g., the abdomen, to provide a working area for the surgeon. After the abdomen is insufflated, a trocar device is utilized to puncture the peritoneum to provide an access port by way of a cannula through the abdominal wall for the introduction of surgical instrumentation. Generally, a trocar/cannula is placed through the abdominal wall for each piece of surgical instrumentation which is necessary to carry out the surgical procedure. In this manner, the surgeon may view the surgical site through an endoscope provided through a first trocar/cannula, and utilize a second trocar/cannula to introduce a surgical instrument such as a grasper, scissor, clip applier, stapler and any other surgical instrument which may be necessary during the particular surgical procedure.

Although the insufflation gas expands the abdomen to permit the surgeon to view the surgical site, it is often necessary to manipulate the internal organs or tissues to provide a clear path to the surgical objective. In the past, grasping tools have been utilized which pull on the organs or tissues to move them out of the way to provide a clear visual path for the surgeon. Endoscopic retractor mechanisms also have been developed which are utilized to push and hold the tissue or organs away from the surgical site. Typically, these devices include paddles and/or fingers which expand after the retractor has been inserted into the abdomen through the trocar cannula. Such devices are disclosed in, for example, U.S. Pat. No. 4,654,028 to Suma, U.S. Pat. No. 4,909,789 to Taguchi et al., and U.S. Pat. No. 5,195,505 to Josefsen. Other retractor devices include collapsible fingers joined by webs of resilient material which expand to form the retractor. These devices are disclosed in, for example, U.S. Pat. No. 4,190,042 to Sinnreich and U.S. Pat. No. 4,744,363 to Hasson. Other devices include retractors having expandable frames for supporting expandable latex sheaths or covers, such as those described in U.S. Pat. No. 5,178,133 to Pena Current endoscopic retractors are typically based on a 10 mm instrument diameter platform. Accordingly, some minimally invasive surgical procedures have limitations due to the small internal diameter of many commonly used cannulas of trocar systems. However, as with most endoscopic instruments, if possible, a smaller diameter retraction device is preferred in order to reduce the amount of trauma to the patient. For example, many surgical procedures now utilize surgical devices based on a 5 mm instrument diameter platform. However, when using smaller diameter retraction devices, the amount of deflection at the distal end of the smaller diameter retraction device is relatively greater than the amount of deflection at the distal end of a larger diameter retraction device. This increased deflection is undesirable when attempting to retract body organs since the smaller diameter retraction device will have difficulty in clearing the surgical field to provide access for the surgeon to the surgical site.

Accordingly, a need exists for an endoscopic organ retraction system having sufficient strength and durability to retract body organs from the operative site and, more particularly, to an endoscopic organ retraction system which is relatively small and may be utilized with smaller conventional trocar cannulas to provide access to the site during an endoscopic or laparoscopic surgical procedure.

The device disclosed herein overcomes the disadvantages associated with the prior art and provides a light weight endoscopic retractor which allows the surgeon to manipulate body organs and other body tissue.

SUMMARY

The presently disclosed retraction system overcomes many of the disadvantages of prior art retractors by providing a retractor device which increases the control over sections thereof, such as, for example, the distal end of the retractor device, as well as providing greater retractive strength as compared to other retractor devices. In addition to providing greater retractive strength, the presently disclosed retractor system is particularly useful in connection with smaller diameter surgical instrument platforms, such as, for example, 5 mm diameter instrument platforms.

A retraction system includes a shaft configured and dimensioned to be inserted into a body cavity, a retractor device operatively associated with the shaft, the retractor device having a first configuration for insertion into the body cavity and at least a second configuration for retraction of the body organ, and at least one securement member operatively coupled to the retractor device for securing the retractor device to a wall of the body cavity.

The at least one securement member includes at least one suture operatively coupled to the retractor device. The at least one securement member can include a plurality of sutures operatively coupled to the retractor device. The retraction system can further include a plurality of anchors operatively couplable to the at least one suture, wherein each anchor is configured and adapted to anchor the sutures with respect to the wall of the body cavity. The at least one suture extends through the shaft.

In one embodiment, the retractor device includes a pair of resilient bands having distal ends operatively connected to one another, the bands being movable between an open position forming a retracting surface and a closed position. The retractor device can be selectively removably associated with the shaft. The shaft desirably defines a lumen and the retractor device can be positioned within the lumen when the retractor device is in the closed position. Desirably, the retractor device includes a sheath surrounding the resilient bands. At least one securement member can extend from each of a distal end and a proximal end of the retractor device.

In another embodiment, the retractor device is a sling having a pair of opposed ends. The at least one securement member includes at least one suture extending from the sling. The shaft desirably defines a lumen such that the sling can be positioned within the lumen.

According to another embodiment, the retractor device can be operatively connected to the shaft at a distal end of the elongate shaft, preferably to a location along a length of the shaft. The at least one securement member can be a suction device operatively connected to a distal end of the securement shaft. The suction device is desirably configured and adapted to transmit a vacuum effect to the wall of the body cavity. The retraction system further includes a source of vacuum operatively connected to the suction device. The retractor device includes a plurality of blade members movable to a fanned-out position.

The present disclosure is also directed to a method of retracting. The method includes the step of inserting a retraction system having a retraction device and a securement member into a body cavity through an insertion point on a first side of the body cavity when the retraction device in the first configuration. The insertion point is preferably located at a position which is spaced a longitudinal distance from a transverse plane defined by a body organ and/or tissue to be retracted.

The method further includes the steps of securing the at least one securement member to a wall of the body cavity opposite the first side, the at least one securement member being secured to the wall at a position spaced a longitudinal distance from the transverse plane, and urging the retractor device against the body organ and/or tissue so as to displace the body organ and/or tissue in the longitudinal direction.

It is envisioned that the securement member is a suture having a first end extending from a distal end of the retractor device, the method further comprising advancing the suture to the wall of the body cavity opposite the first side. The suture includes a second end extending through a shaft, and the step of urging includes tensioning the suture.

It is contemplated that the retractor device includes a pair of resilient bands, the bands being movable between an open position forming a retracting surface and a closed position, and the method includes deploying the retractor device to the open position.

It is envisioned that the retraction system has a shaft which is removable from the suture and the retractor device. Accordingly, the method includes the step of removing the shaft.

The retraction system desirably includes a shaft defining a lumen. Accordingly, the method includes deploying the retractor device by releasing the retractor device from the lumen.

It is envisioned that the retractor device includes a sheath surrounding the resilient bands. The shaft can be withdrawn after the at least one securement member is secured to the wall. It is further envisioned that the retractor device is a sling having a pair of opposed ends, and the method includes disposing the sling around the body organ and/or body tissue.

Desirably, the at least one anchor member includes at least one suture extending from each opposed end of the sling, and the step of urging includes manipulating the at least one suture.

It is envisioned that the at least one securement member is a suction device operatively connected to a distal end of a shaft. As such, the method of securing includes the step of activating the suction device.

The retraction device includes a plurality of blade members. Accordingly, the method includes deploying the blade members to a fanned-out position.

The presently disclosed retraction systems and methods, together with attendant advantages, will be best understood by reference to the following detailed description in conjunction with the figures below.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
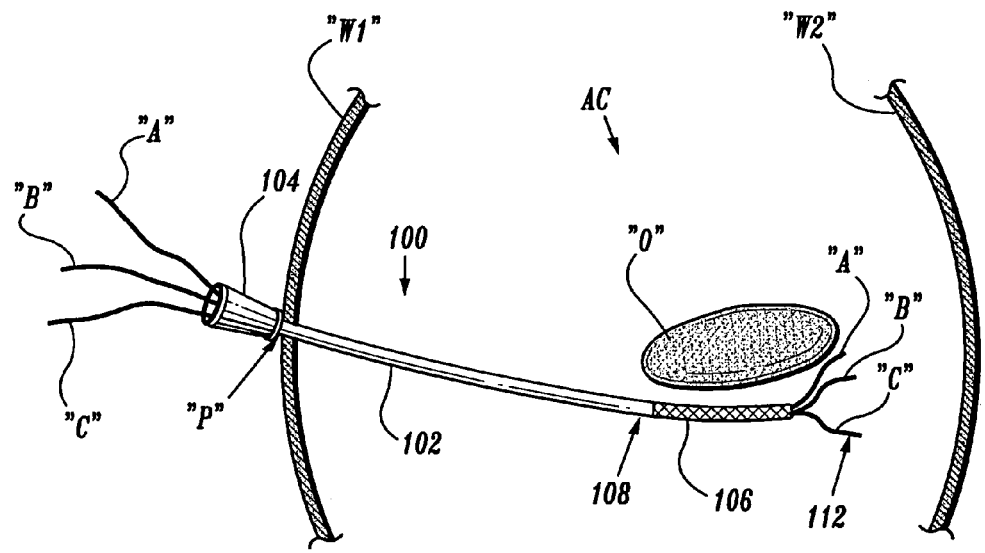
FIG. 1 is a schematic illustration of a method of using a retraction system, in accordance with an embodiment of the present disclosure.
Figure 2:
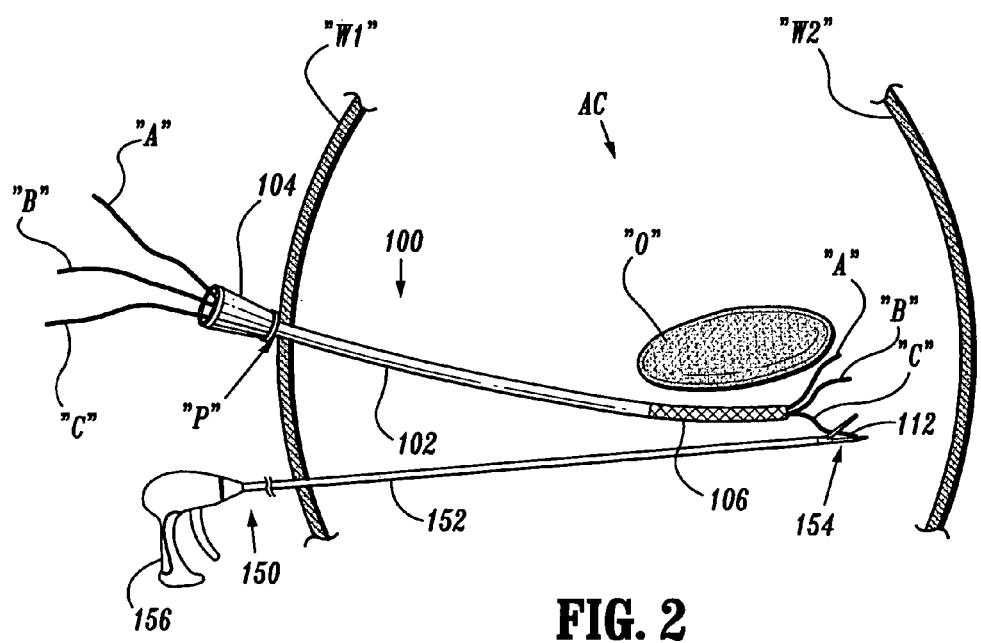
FIG. 2 is a schematic illustration of a method in accordance with the embodiment of FIG. 1, at a later stage in the method.

Referring initially to FIGS. 1–5, an illustrative example of an endoscopic retraction system, in accordance with the present disclosure, is shown generally as retraction system 100 which includes an elongate shaft 102 extending distally from a handle portion 104. Elongate shaft 102 and handle 104 include a lumen (not shown) extending completely therethrough. Retraction system 100 further includes a retractor device 106 operatively connected to a distal end 108 of shaft 102. While it is preferred that retractor device 106 is positioned at distal end 108 of shaft 102, it is envisioned that retractor device 106 can be disposed and/or located at any location along shaft 102, between handle portion 104 and distal end 108.

Retractor device 106 is deployable from a first configuration, e.g., closed configuration (see FIGS. 1 and 2), for insertion of retraction system 100 into an abdominal cavity "AC" through an abdominal wall "W1" and/or removal of retraction system 100 through abdominal wall "W1", to a second configuration, e.g., partially or fully opened configuration (see FIGS. 3, 4 and 5), for retraction of body tissue, including an internal body organ "O" (e.g., a liver). Manipulation of retractor device 106 from the first to the second configuration and back again can be accomplished manually or automatically by operatively coupling an expansion mechanism to handle portion 104 for remote deployment.

An example of a retractor device or paddle including deployment mechanism may be found in commonly assigned U.S. Pat. No. 5,656,012 to Sienkiewicz, the disclosure of which is hereby incorporated by reference herein. Briefly, Sienkiewicz discloses in certain embodiments thereof a surgical retractor having a handle portion, an elongated body portion extending distally from the handle portion and including an outer tube, a fixed stabilizing member extending from a distal end of the outer tube and a pair of resilient bands pivotally connected to a distal end portion of the stabilizing member. An actuation mechanism is provided which is associated with the handle portion and proximal end portions of the bands for moving the bands between open and closed positions. The surgical retractor of Sienkiewicz further includes a sheath dimensioned to receive at least a portion of the stabilizing member and the bands. Accordingly, when the bands are deployed, the sheath is expanded so as to define a retracting surface for manipulating body tissue and organs during a laparoscopic or endoscopic surgical procedure.

Alternatively, retractor device 106 may be formed as any other suitable expandable retractor, such as, for example, multiple deployable blades. An example of such an expandable retractor including a deployment mechanism is disclosed in commonly assigned U.S. Pat. No. 5,456,695 to Herve-Dallemange, the disclosure of which is hereby incorporated by reference herein. Briefly, Herve-Dallemange discloses, in certain embodiments thereof, a multi-tool surgical apparatus including a handle assembly and a body portion which extends from the handle assembly. The multi-tool surgical instrument further includes a first tool means operatively associated with a distal end portion of the body portion for performing a first surgical task, and second tool means operatively associated with a medial section of the body portion for performing a second surgical task. Herve Dallemange discloses that the second tool means is a plurality of interleaved cooperating blade members which are movable between an open position and a closed position for performing retraction tasks during a surgical procedure.

Any deployment mechanism may be used. For example, U.S. Pat. No. 5,656,012 to Sienkiewicz, the disclosure of which is hereby incorporated by reference herein, discloses in certain embodiments a deployment mechanism comprising a rotatable knob operatively associated with a central rod. The central rod is slidably disposed with respect to a stabilizing member. Resilient bands have a proximal end attached to the central rod and a distal end attached to the stabilizing member. Rotation of the knob moves the central rod distally, expanding the resilient bands. The resilient bands form a surface for retracting tissue within the patient's body. The deployment mechanism disclosed in certain embodiments of U.S. Pat. No. 5,456,695 to Herve Dallemange may also be used. Blade members are deployed through interaction with a drive screw assembly. The blade members are engaged with a pin attached to a drive bar. The drive bar moves in a distal direction to deploy the blade members to a fanned-out configuration. The drive bar is attached to the drive screw assembly through a pin at a proximal end of the drive bar. The drive screw assembly has a threaded exterior surface for interaction with the threaded interior surface of a rotatable knob. The drive screw assembly translates in a distal direction on a guide tube in response to rotation of the knob, causing distal movement of the drive bar and deployment of the blade member. In further embodiments, the retractor is self-deployable. The retractor comprises resilient members biased to an expanded position within a sleeve. The resilient members may comprise a material biased to the expanded position or a separate biasing element, such as a spring, may be provided. In further embodiments, sutures may be used as a deployment mechanism. Desirably, the deployment mechanism deploys and collapses the retractor device. The deployment mechanism may be detachable from the retractor device.

Retractor device 106 may be of a variety of different types, for example, paddle-forming expandable elongated elements, balloon, solid surface, etc. and can be manufactured in a variety of fashions. For example, retraction system 100 can be completely disposable or include a removable retractor device 106, which is disposable, and a reusable handle portion 104.

Figure 3:
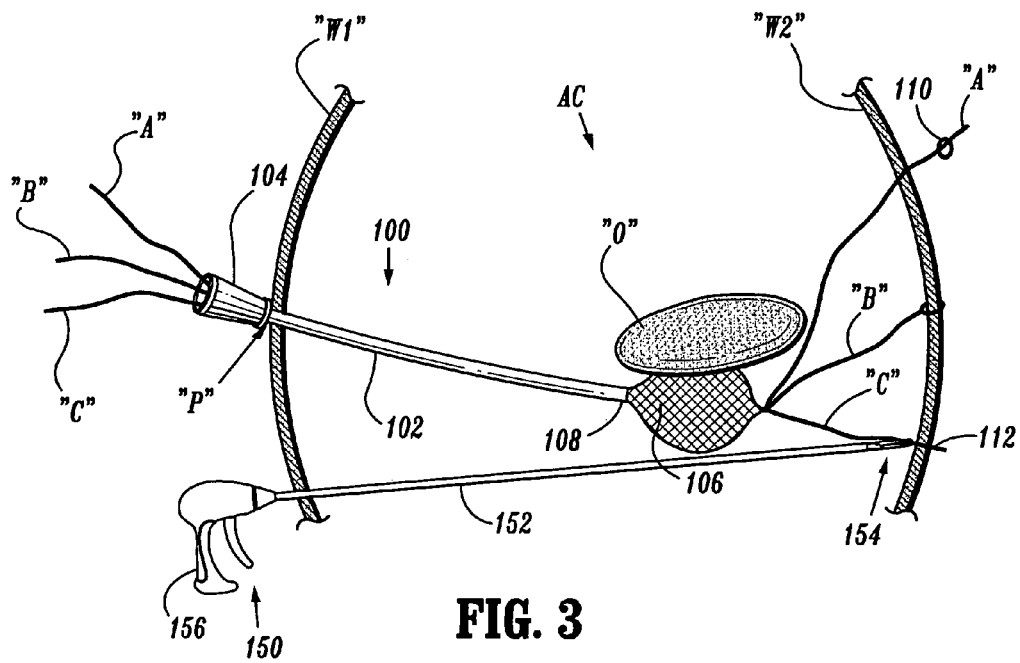
FIG. 3 is a schematic illustration of a method in accordance with the embodiment of FIGS. 1–2, at a later stage in the method.
Figure 4:
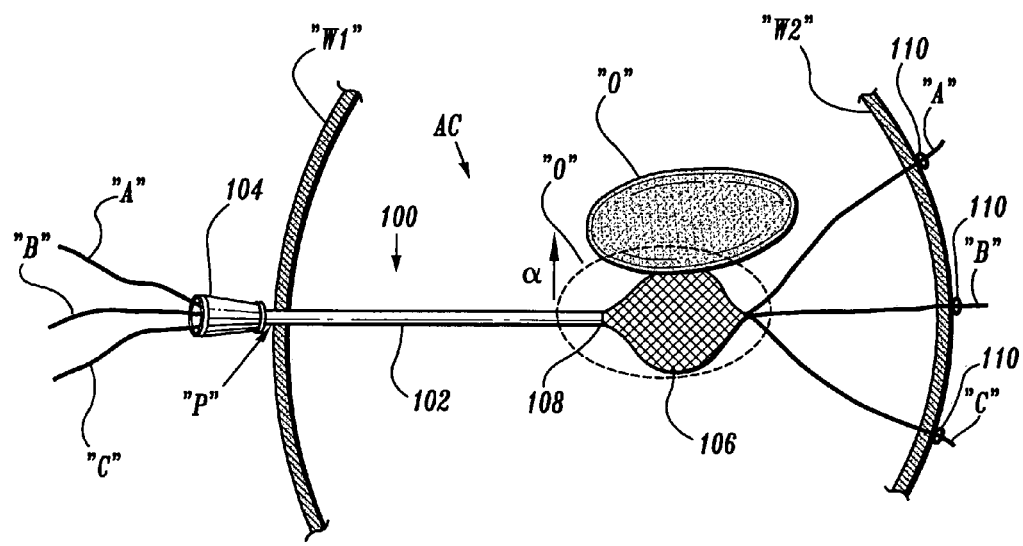
FIG. 4 is a schematic illustration of a method in accordance with the embodiment of FIGS. 1–3, at a later stage in the method.
Figure 5:
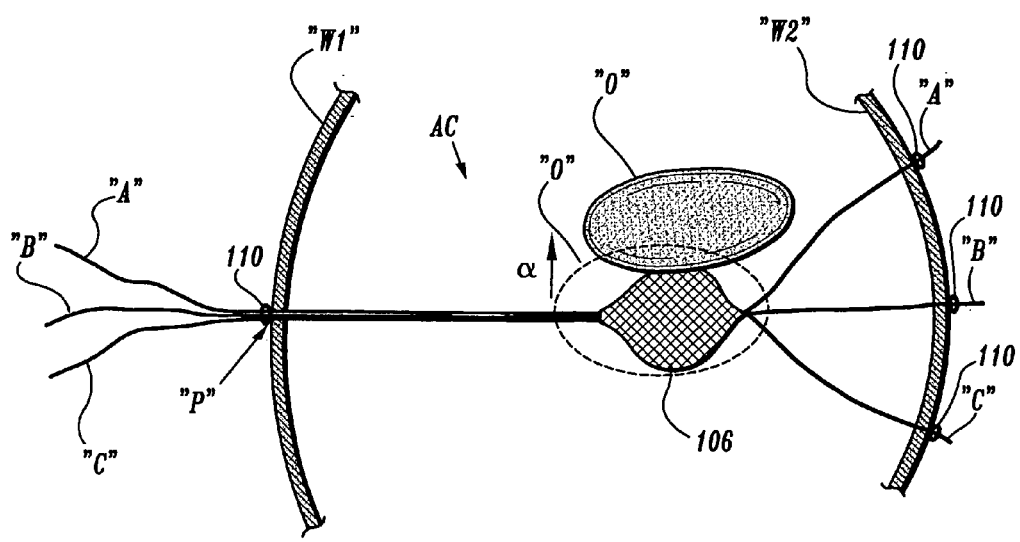
FIG. 5 is a schematic illustration of a method in accordance with the embodiment of FIGS. 1–3 and 4, at a later stage in the method.

In accordance with the present disclosure, retraction system 100 further includes at east one control member, preferably a number of elongated control members. For illustrative purposes only, as shown in FIGS. 1–5, retraction system 100 includes three sutures "A, B and C" operatively associated with retractor device 106. However, it is envisioned that, depending on the particular surgical procedure, retraction system 100 can include more or less sutures as desired and/or needed. As seen in FIGS. 3–5, sutures "A, B and C" are preferably attached to a distal end of retractor device 106, however, it is envisioned that sutures "A, B and C" can extend from any location along the outer surface of retractor device 106 depending upon the desired manipulation required of retraction system 100 desired. In one preferred embodiment, it is envisioned that each suture "A, B and C" is provided with a needle 112 (FIGS. 1–3) at a distal end thereof.

It is envisioned that, depending on the particular surgical procedure, that retraction system 100 will include more or less sutures as needed. It is further envisioned that sutures "A, B and C" are adapted to be secured to an opposed abdominal wall "W2". In one method, as seen in FIG. 3, a grasping tool 150 is provided for pushing the individual sutures "A, B and C" through abdominal cavity "AC". Preferably, grasping tool 150 includes an elongate shaft 152 having a jaw mechanism 154 operatively coupled to a distal end thereof and a trigger mechanism 156 operatively coupled to a proximal end thereof for manipulating jaw mechanism 154. In use, grasping tool 150 is used to enter abdominal cavity "AC" through an abdominal wall "W1", on the same side from which retraction system 100 is inserted into abdominal cavity "AC", grasps a needle 112 of one of sutures "A, B and C" and extends and/or pushes needle 112 and suture "A, B or C" across abdominal cavity "AC" to secure suture "A, B or C" to opposite abdominal wall "W2". This step is repeated for each suture "A, B and C".

Figure 3A:
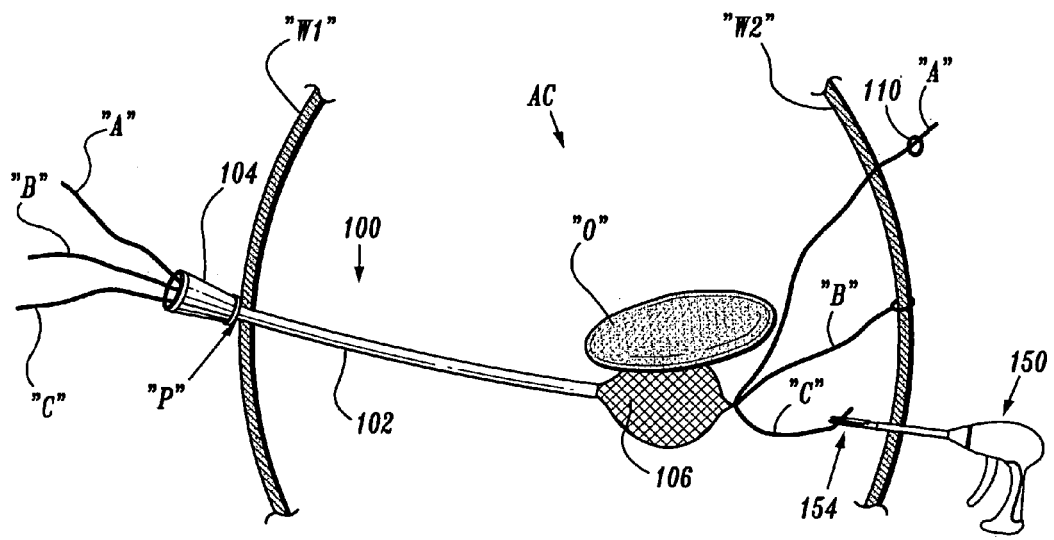
FIG. 3A is a schematic illustration of the retraction system of FIGS. 1–2 depicting an alternative method of using the retraction system.

Alternatively, as seen in FIG. 3A, it is envisioned that grasping tool 150 can be used to enter abdominal cavity "AC" through abdominal wall "W2", on a side opposite abdominal wall "W1" from which retraction system 100 enters abdominal cavity "AC", grasps a needle 112 of one of sutures "A, B and C" and pulls and/or withdraws needle 112 and suture "A, B or C" across abdominal cavity "AC" to secure suture "A, B or C" to abdominal wall "W2".

If no needles 112 are provided on the distal ends of sutures "A, B and C", sutures "A, B and C" can be pulled through abdominal wall "W2" using an endoscopic grasping or suturing device such as, for example, an ENDO-CLOSE™ instrument available from United States Surgical, a division of Tyco Healthcare Group LP, Norwalk, Conn. Reference can be made to commonly assigned U.S. Pat. No. 5,281,237, the disclosure of which is hereby incorporated by reference herein, for a detailed description of an exemplary ENDO-CLOSE™ instrument.

As shown in FIGS. 3 and 3A, it is contemplated that retraction system 100 can be provided with a plurality of anchors 110 which can be coupled, one each, to a respective distal end of sutures "A, B and C" after sutures "A, B and/or C" are passed through abdominal wall "W2". In particular, in accordance with the present disclosure, once a suture "A, B or C" is pulled out of abdominal cavity "AC", through abdominal wall "W2", an anchor 110 is coupled to the end of each suture "A, B or C" in order to prevent the suture "A, B or C" from being pulled back into abdominal cavity "AC". Preferably, anchors 110 are positioned in contact with the outer surface of abdominal wall "W2" in order to maintain sutures "A, B or C" in tension. In this manner, sutures "A, B and C" are essentially anchored to abdominal wall "W2". As understood and used herein, anchors 110 include, but are not limited to, clamps, clips, staples, rods, knots and the like. Anchors 110 may comprise any device for securing the sutures to the abdominal wall, including devices that attach to or otherwise engage the abdominal wall.

In one embodiment, it is envisioned that the proximal ends of sutures "A, B and C" pass through retractor device 106 and through the lumen of shaft 102 and handle 104 in order to exit abdominal cavity "AC" through abdominal wall "W1". In this manner, after sutures "A, B and C" have been anchored to abdominal wall "W2", retractor device 106 and elongate shaft 102 can be slid into position, along sutures "A, B and C". Accordingly, as seen in FIG. 5, handle 104 and shaft 102, if desired, can be withdrawn from abdominal cavity "AC" and the proximal ends of sutures "A, B and C" can be stitched to abdominal wall "W2" or at least anchored to abdominal wall "W2" by a anchor 110 to thereby secure sutures "A, B and C" in place.

With continuing reference to FIGS. 1–5, a preferred method of using retraction system 100 will now be described. In use, retraction system 100 is configured and adapted to retract a body organ "O" in a direction "α" (FIGS. 4 and 5) in order to provide a surgeon with an enlarged space and increased room to operate. Accordingly, retractor device 106 of retraction system 100 is inserted into abdominal cavity "AC" through an insertion point "P" formed in abdominal wall "W1", at a location in a direction "α" relative to a plane extending through body organ "O" and oriented transversely to direction "α". Retraction system 100 is advanced toward body organ "O" such that a distal end of shaft 102 is in close proximity to body organ "O". In other words, insertion point "P" of retraction system 100 is preferably at a location which is spaced a longitudinal distance (e.g., in the direction opposite "α") from the transverse plane. It is envisioned and within the scope of the present disclosure to have a trocar system (not shown) operatively disposed at insertion point "P" which in turn provides access to abdominal cavity "AC" through abdominal wall "W1". Desirably, abdominal cavity "AC" is insufflated and the trocar system or other port is arranged to maintain insufflation.

Sutures "A, B and C" are then secured to or pulled through opposite abdominal wall "W2" using known surgical techniques or by using a method as described above. Preferably, sutures "A, B and C" are pulled through abdominal wall "W2" at locations spaced a longitudinal distance, in the direction "α", from the transverse plane extending through body organ "O".

Retractor device 106 is then deployed (i.e., manipulated from the first configuration to the second configuration) in order to increase the surface area against which body organ "O" contacts. With retractor device 106 deployed to the second configuration and in position, anchors 110 can be coupled to sutures "A, B and C" at a location adjacent the exterior surface of abdominal wall "W2" or sutures "A, B and C" can be otherwise secured to abdominal wall "W2" in order to prevent sutures "A, B and C" from slipping or being withdrawn back into abdominal cavity "AC". Sutures "A, B and C" are then tensioned by withdrawing and/or pulling on the proximal ends of sutures "A, B and C" (i.e., the portion of sutures "A, B and C" extending out of abdominal cavity "AC" through abdominal wall "W1"). Tensioning of sutures "A, B and C" causes retractor device 106, as well as body organ "O", to be moved and/or urged in direction "α". The proximal end of shaft 102 may be secured externally or may be secured to abdominal wall "W1". In accordance with the present disclosure, sutures "A, B and C" effectively provide support to the distal end of shaft 102 by being secured to abdominal wall "W2". Accordingly, the tendency of the distal end of shaft 102 to deflect during retraction of body organ "O" will be reduced as compared to an organ retractor having an unsupported distal end. An external support may be connected to sutures A, B and C and/or connected to the proximal end of the shaft 102 and handle 104.

Preferably, as described above, insertion point "P" for retraction system 100 through abdominal wall "W1", and the points in abdominal wall "W2" through and/or to which sutures "A, B and C" pass and/or are secured to are selected such that when sutures "A, B and C" are tensioned, retractor device 106 as well as body organ "O" will move and/or be urged in direction "α".

Following the surgical procedure, the tension on sutures "A, B and C" can be removed thereby allowing body organ "O" to return substantially to its original position in abdominal cavity "AC". Sutures "A, B and C" are then released from abdominal wall "W2" and retractor device 106 manipulated to the first configuration so that retraction system 100 can be withdrawn from abdominal cavity "AC".

It is envisioned that elongate shaft 102 can be provided with a locking mechanism (not shown) for selectively fixing the position of sutures "A, B and C" extending through the lumen thereof. In certain embodiments, as discussed above, shaft 102 and handle 104 are detached and removed and the sutures are secured to insertion point "P".

Figure 6A:
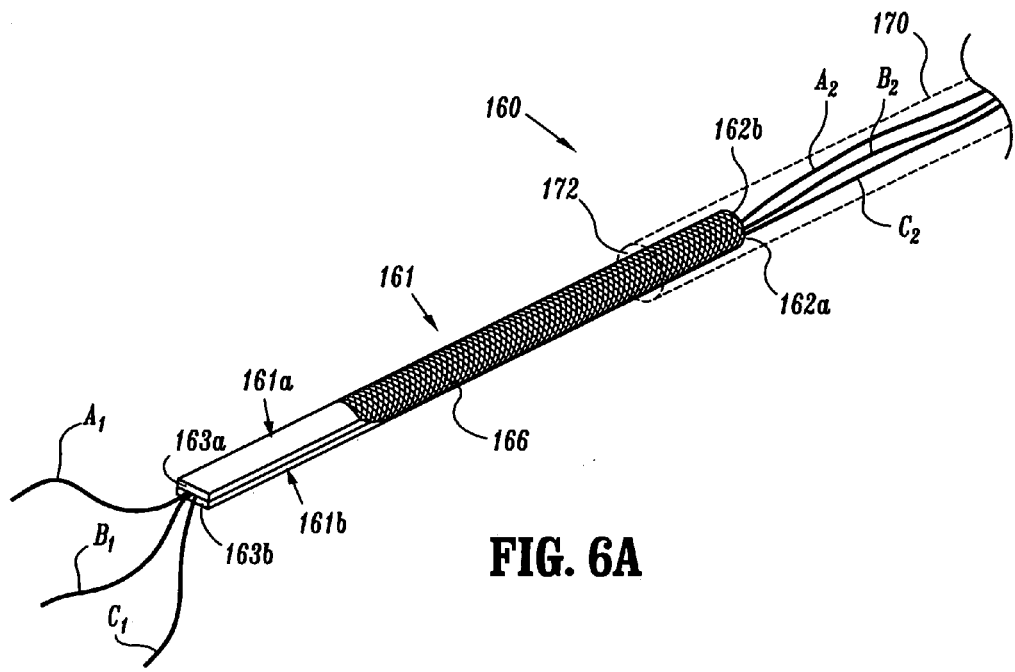
FIG. 6A is an enlarged perspective view of a retractor device, shown in a first configuration, according to an alternative embodiment of the present disclosure.
Figure 6B:
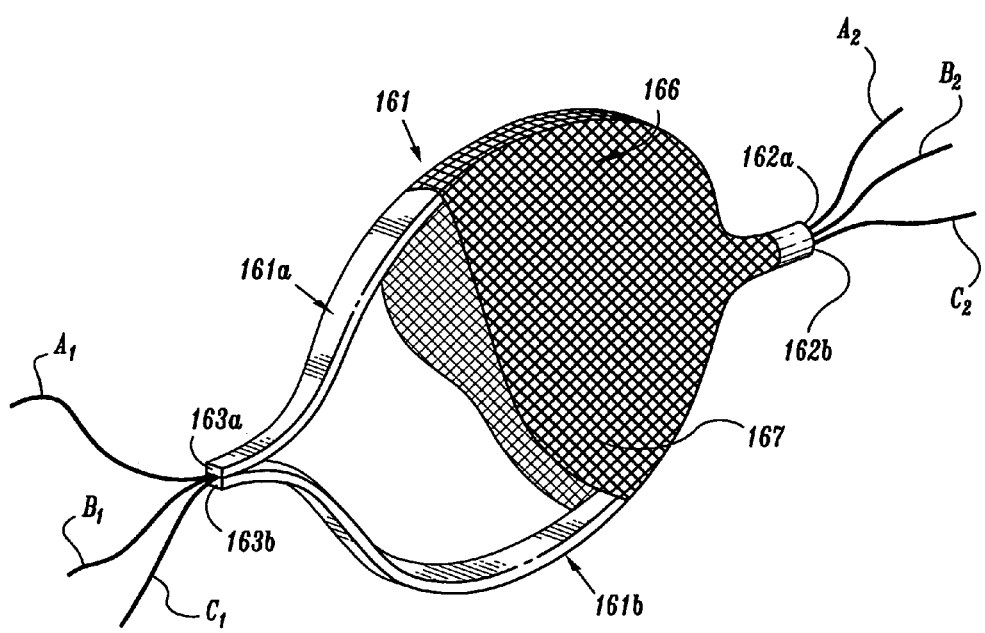
FIG. 6B is an enlarged perspective view of the retractor device of FIG. 6A shown in a second configuration.

Turning now to FIGS. 6A and 6B, a retraction system in accordance with another embodiment of the present disclosure is shown generally as 160. It is envisioned that retraction system 160 includes a refractor device 161 which operates in combination with an elongate insertion tube 170 (shown in phantom in FIG. 6A) defining a lumen 172 therethrough. It is envisioned that retractor device 161 is slidingly receivable in lumen 172 of insertion tube 170.

As seen in FIGS. 6A and 6B, retractor device 161 is deployable from a first configuration, e.g., closed configuration (see FIG. 6A), during passage of insertion tube 170 into abdominal cavity "AC" through abdominal wall "W1" and/or removal of retractor device 161 from abdominal cavity "AC", to a second configuration, e.g., partially or fully opened configuration (see FIG. 6B), during retraction of an internal body organ "O" (e.g., a liver). Deployment of retractor device 161 from the first to the second configuration is preferably accomplished automatically as will be described in greater detail below.

Desirably, as seen in FIGS. 6A and 6B, retractor device 161 includes a pair of resilient band members 161a, 161b fixedly secured to one another at proximal ends 162a, 162b, respectively, and at distal ends 163a, 163b, respectively. Resilient bands 161a, 161b are preferably formed of stainless steel or other flexible material, such as shape memory alloy or a flexible polymer, the configuration of which can be controlled mechanically by applying a stress thereto. In the present embodiment, resilient bands 161a, 161b are movable between the second configuration (i.e., open or deployed configuration) and the first configuration (i.e., closed or retracted configuration). In the second configuration each resilient band 161a, 161b preferably has an arcuate configuration while in the first configuration each resilient band 161a, 161b is substantially planar and/or linear. Each resilient band 161a, 161b is preferably fabricated to have a rectangular cross-sectional profile to thereby strengthen each band 161a, 161b. Alternatively, each band 161a, 161b can have a semi-circular cross-sectional profile or any other suitable cross-sectional profile.

Retractor device 161 further includes an expandable sheath 166 preferably configured and dimensioned to substantially surround resilient bands 161a, 161b. Alternatively, it is envisioned that sheath 166 can be secured to each of the juxtaposed surfaces of resilient bands 161a, 161b. Expandable sheath 166 is preferably fabricated from a textile material such as surgical mesh, cloth, nylon, etc. Alternatively, sheath 166 can be fabricated from an elastomeric material such as, for example, latex. Accordingly, when retractor device 106 is in the second configuration, sheath 166 is expanded (i.e., stretched out over resilient bands 161a, 161b so as to define a retracting surface 167 for manipulating body tissue and organs during laparoscopic and/or endoscopic surgical procedures.

In accordance with the present disclosure, retractor device 161 further includes a 15 first set of sutures "$A_1$, $B_1$ and $C_1$" attached to a distal end thereof and a second set of sutures "$A_2$, $B_2$ and $C_2$" attached to a proximal end thereof. It is envisioned and understood that sutures "A, B and C" may extend from retractor device 161 at any location along the outer surface thereof depending upon the desired manipulation required and/or desired a given surgical procedure.

It is envisioned that the same sutures "A, B and C" can extend through retractor device 161 and extend from both the distal end and the proximal end. It is further envisioned that retractor device 161 can be slidable along the length of sutures "A, B and C".

Sutures "$A_1$, $B_1$ and $C_1$" can be pulled or pushed through abdominal wall "W2" using an endoscopic grasping or suturing device, such as, for example, the ENDO-CLOSE™ instrument as described above. It is contemplated that a plurality of stops or anchors 110 can be provided which can be coupled, at least one each, to a distal end of each suture "$A_1$, $B_1$ and $C_1$" after sutures "$A_1$, $B_1$, and/or $C_1$" have been passed through abdominal wall "W2".

Figure 7A:
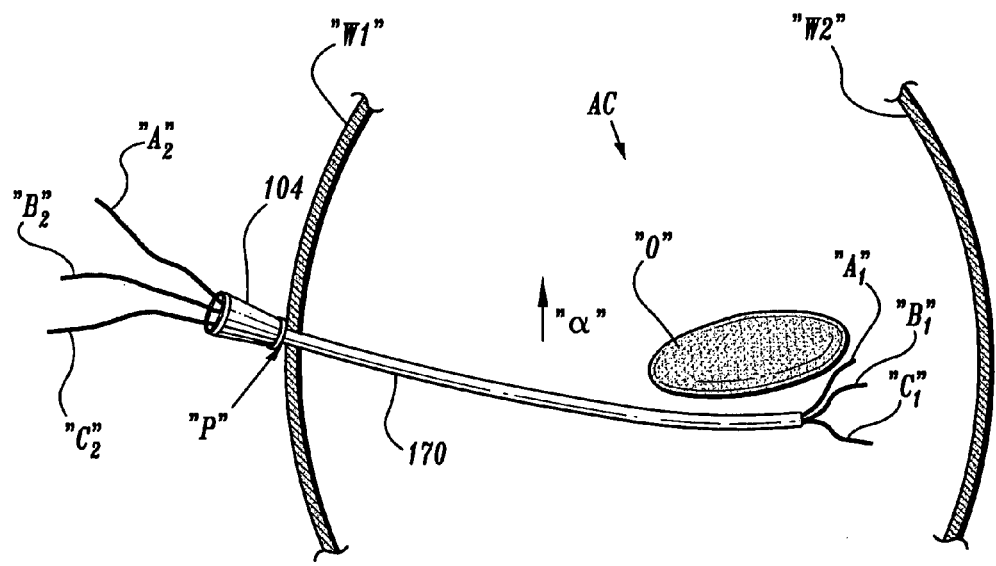
FIG. 7A is a schematic illustration of a method of using a retraction system, in accordance with another embodiment of the present disclosure.
Figure 7B:
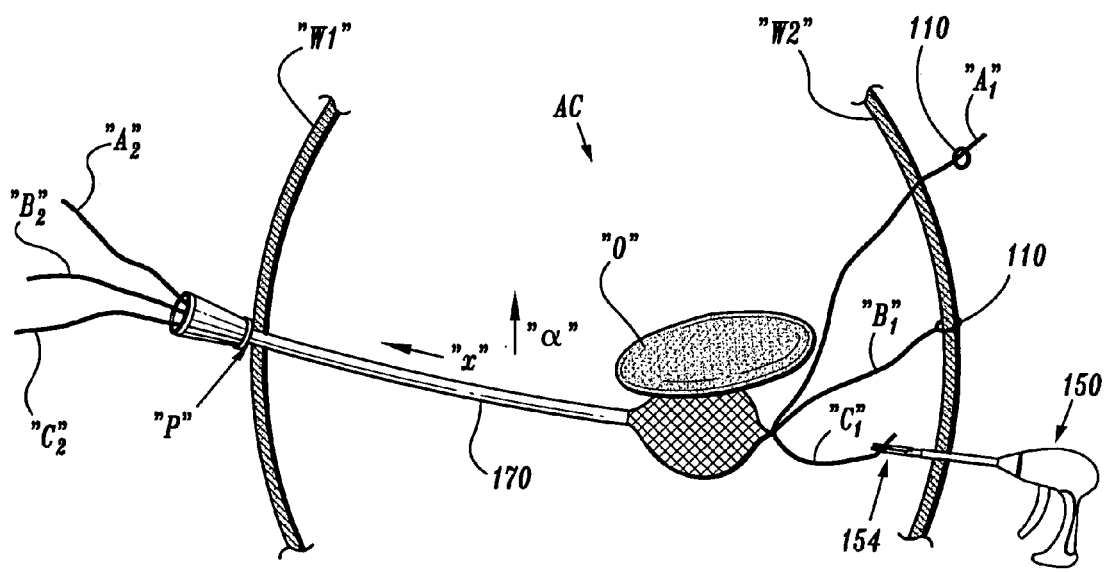
FIG. 7B is a schematic illustration of a method of using a retraction system in accordance with the embodiment of FIG. 7A at a later stage in the method.
Figure 7C:
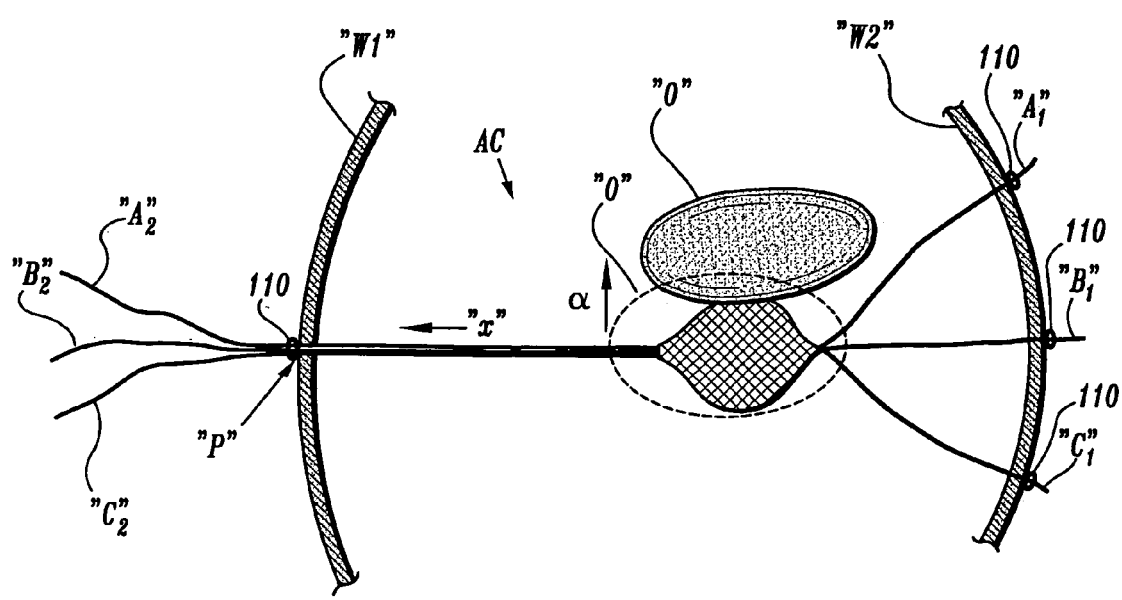
FIG. 7C is a schematic illustration of a method in accordance with the embodiment of FIGS. 7A–7B, at a later stage in the method.

In use, as seen in FIGS. 7A–7C, retractor device 161 is in the first position and slidably disposed in lumen 172 of insertion tube 170. Desirably, abdominal cavity "AC" is insufflated and a trocar system or other port used to maintain insufflation. Preferably, sutures "$A_1$, $B_1$ and $C_1$" extend out a distal end of insertion tube 170 and insertion tube 170 is inserted, through insertion point "P" formed in abdominal wall "W1", into abdominal cavity "AC" at a location with respect to a direction "α" relative to a plane extending through body organ "O" and oriented transversely to direction "α". Sutures "$A_1$, $B_1$ and $C_1$" are secured to abdominal wall "W2" in the same manner as sutures "A, B and C" of retraction system 100 described above. Preferably, as seen in FIG. 7B, sutures "$A_1$, $B_1$ and $C_1$" are secured to abdominal wall "W2" and desirably spaced in the direction "α" relative to the transverse plane. Desirably, sutures "$A_1$, $B_1$ and $C_1$" are secured to abdominal wall "W2", with anchors 110, such that sutures "$A_1$, $B_1$ and $C_1$" have a length which places the distal end of insertion tube 170 in close proximity to body organ "O".

Alternatively, it is envisioned that each suture "$A_1$, $B_1$ and $C_1$" is provided with a needle 112 at a distal end thereof. In this manner, sutures "$A_1$, $B_1$ and $C_1$" can be secured to abdominal wall "W2" in the same manner as described above with regard to retractor device 106.

As seen in FIG. 7B, with sutures "$A_1$, $B_1$ and $C_1$" anchored to abdominal wall "W2", insertion tube 170 is withdrawn in a direction "X" thereby causing retractor device 161 to be pulled from insertion tube 170 and deployed to the second configuration in the proximity of body organ "O". In certain embodiments, as seen in FIG. 7C, insertion tube 170 is completely withdrawn from abdominal cavity "AC" such that sutures "$A_2$, $B_2$ and $C_2$" extend out of insertion point "P". Sutures "$A_2$, $B_2$ and $C_2$" are then pulled and/or tensioned, in direction "X", to thereby move and/or urge body organ "O" in direction "α". Sutures "$A_2$, $B_2$ and $C_2$" can then be secured to abdominal wall "W1" in the same manner as sutures "$A_1$, $B_1$ and $C_1$" to hold body organ "O" in the retracted position. In certain embodiments, sutures "$A_1$, $B_1$ and $C_1$" and/or "$A_2$, $B_2$ and $C_2$" are attached to an external support.

Following the surgical procedure, sutures "$A_1$, $B_1$ and $C_1$" are released from abdominal wall "W2" thereby allowing body organ to substantially return to its pre-retracted position. The insertion tube 170 may be re-introduced into abdominal cavity "AC", through insertion point "P". Sutures "$A_2$, $B_2$ and $C_2$" are fed through lumen 172 of insertion tube 170. With sutures "$A_2$, $B_2$ and $C_2$" in place in insertion tube 170, either insertion tube 170 is distally advanced over sutures "$A_2$, $B_2$ and $C_2$" or sutures "$A_2$, $B_2$ and $C_2$" are proximally withdrawn through insertion tube 170. In either manner, proximal ends 162a, 162b of resilient bands 161a, 161b enter lumen 172 of insertion tube 170. The action is continued until resilient bands 161a, 161b are urged to the first position due to a camming action between the distal end of insertion tube 170 and resilient bands 161a, 161b of retractor device 161. Insertion tube 170 can then be fully withdrawn from abdominal cavity "AC" and the surgical procedure completed. In further embodiments, sutures "$A_1$, $B_1$ and $C_1$" and/or "$A_2$, $B_2$ and $C_2$", or additional sutures are used to erge the resilient bands 161a, 161b to the first position.

Referring now to FIGS. 8–12, an alternative embodiment of a retraction system, in accordance with the present disclosure, is shown generally as 200. Retraction system 200 includes a retractor 202 for retracting body organ "O" and an insertion tool 220 for deploying retractor 202. Preferably, as seen in detail in FIGS. 11 and 12, retractor 202 is in the form of a sling or hammock like structure. Insertion tool 220 includes a hollow elongated shaft 222 and a handle portion 224 operatively coupled to a proximal end of shaft 222. Preferably, insertion tool 220 defines a central lumen 221 extending completely through shaft 222 and handle 224. It is envisioned that central lumen 221 of shaft 222 is configured and adapted to receive retractor 202 therein. It is contemplated that shaft 222 can be straight, curved and/or preferably fabricated from a material which is flexible and/or pliable to enable bending of a straight elongate shaft to a curved elongate shaft.

Retractor 202 includes a sling section 204 having a first end 206 and a second end 208 and at least one suture "A" extending between and from ends 206, 208 of sling section 204. The suture "A" may be attached to one or more ends of sling 204 and/or attached at one or more points between the ends. Separate sutures may extend from each of ends 206, 208. As described above with regard to sutures "A, B and C" of retraction system 100, suture "A" of retraction system 200 can be either pushed and/or pulled through abdominal wall "W" using known surgical techniques and instruments, such as, for example, an endoscopic suturing instrument such as the ENDO-CLOSE™ instrument as described above.

It is envisioned that retraction system 200 preferably further includes at least one port 210, i.e., a trocar cannula, configured and adapted to provide access into and out of abdominal cavity "AC" and through which suture "A" can pass and be anchored to. Preferably, port 210 creates an air tight seal around shaft 302 and in abdominal wall "W1" to thereby prevent the escape of insufflation gas from abdominal cavity "AC".

Sling section 204 can be made from a medical grade mesh having sufficient openings to enable access to retracted body organ "O" at various locations along the surface thereof. Preferably, sling section 204 is fabricated from a textile material such as surgical mesh, cloth, nylon, etc. Alternatively, sling section 204 can be fabricated from an elastomeric material such as, for example, latex, polypropylene, polyethylene, etc.

With continued reference to FIGS. 8–12, a preferred method of use of retraction system 200 will now be described. Desirably, abdominal cavity "AC" is insufflated and a trocar system or other port is used to maintain insufflation. In use, retractor system 200 is configured and adapted to retract body organ "O" in direction "α" in order to provide a surgeon with an enlarged space and increased room to operate. Preferably, at least one pair of ports 210 is provided in opposed abdominal walls "W1, W2". It is contemplated that ports 210 are placed at a location which is spaced a longitudinal distance, in direction "α", from a plane defined by body organ "O".

Figure 8:
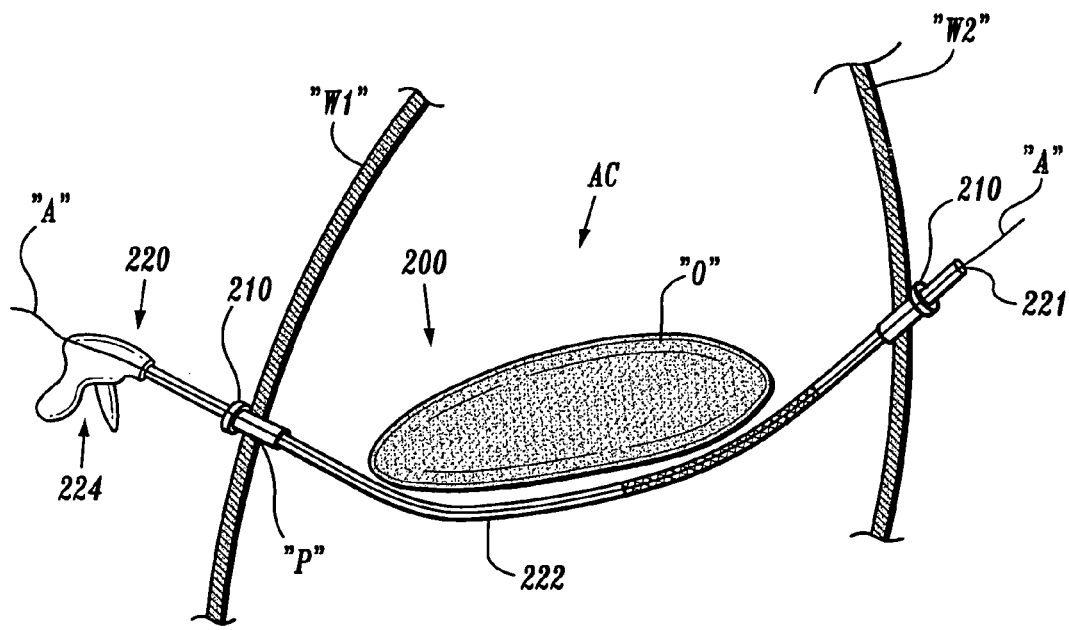
FIG. 8 is a schematic illustration of a method of using a retraction system, in accordance with another embodiment of the present disclosure.
Figure 9:
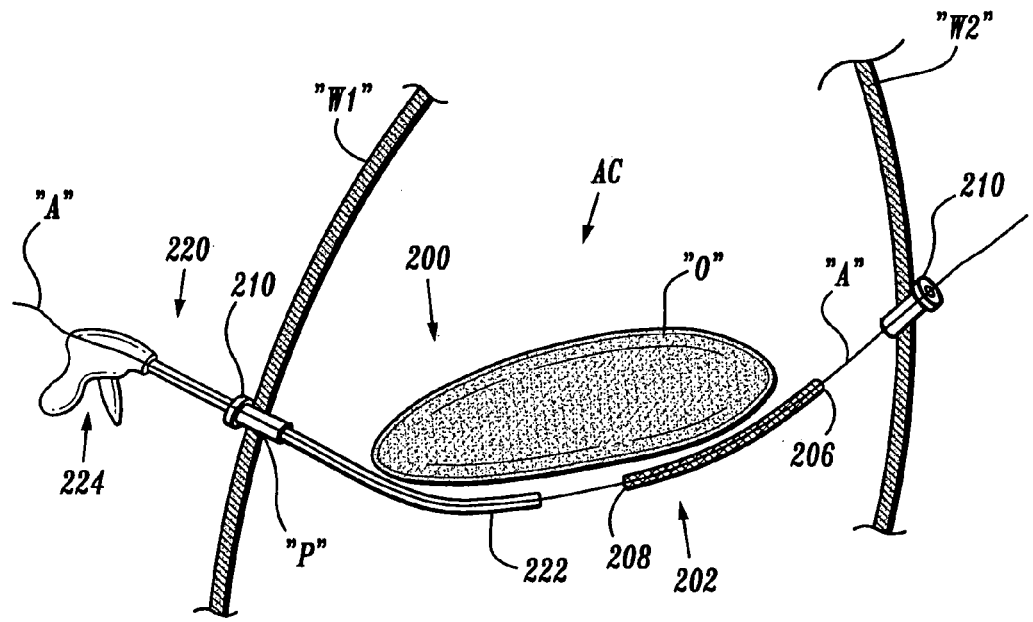
FIG. 9 is a schematic illustration of a method in accordance with the embodiment of FIG. 8, at a later stage in the method.
Figure 10:
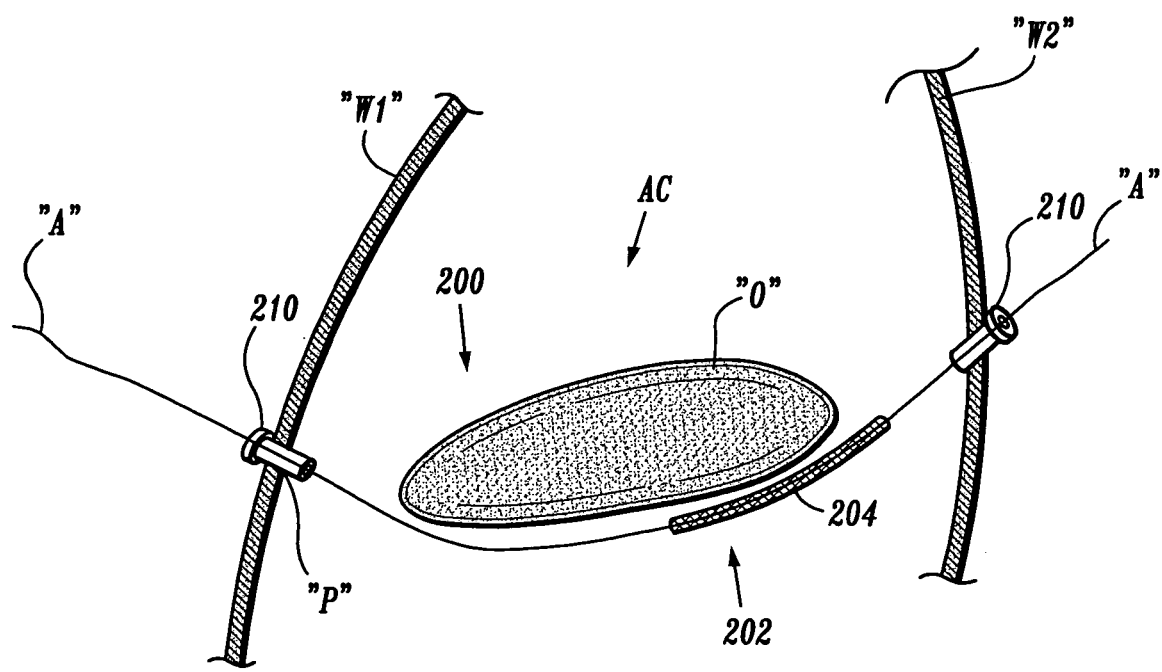
FIG. 10 is a schematic illustration of a method in accordance with the embodiment of FIGS. 8–9, at a later stage in the method.

Shaft 222 of insertion tool 220, having retractor 202 disposed therewithin, is inserted into the abdominal cavity through port 210 disposed in abdominal wall "W1". In accordance with the present disclosure, retractor 202 is disposed within central lumen 221 of shaft 222 such that one end of suture "A" extends from central lumen 221 and out the proximal end of handle 224 and the other end of suture "A" extends from central lumen 221 and out the distal end of shaft 222. Insertion tool 220 is then advanced through the abdominal cavity until the distal end exits abdominal cavity "AC" through port 210 provided in abdominal wall "W2", as seen in FIG. 8. Preferably, shaft 222 is sufficiently bent and deformed in order to pass around/below body organ "O". The distal end of suture "A" is then withheld as insertion tool 220 is withdrawn back through abdominal cavity "AC". In so doing, as seen in FIG. 9, as shaft 222 is withdrawn, retractor 202 is essentially pulled from within central lumen 221 of shaft 222. Preferably, insertion tool 220 is withdrawn until shaft 222 is completely pulled from the abdominal cavity, as seen in FIG. 10.

Figure 11:
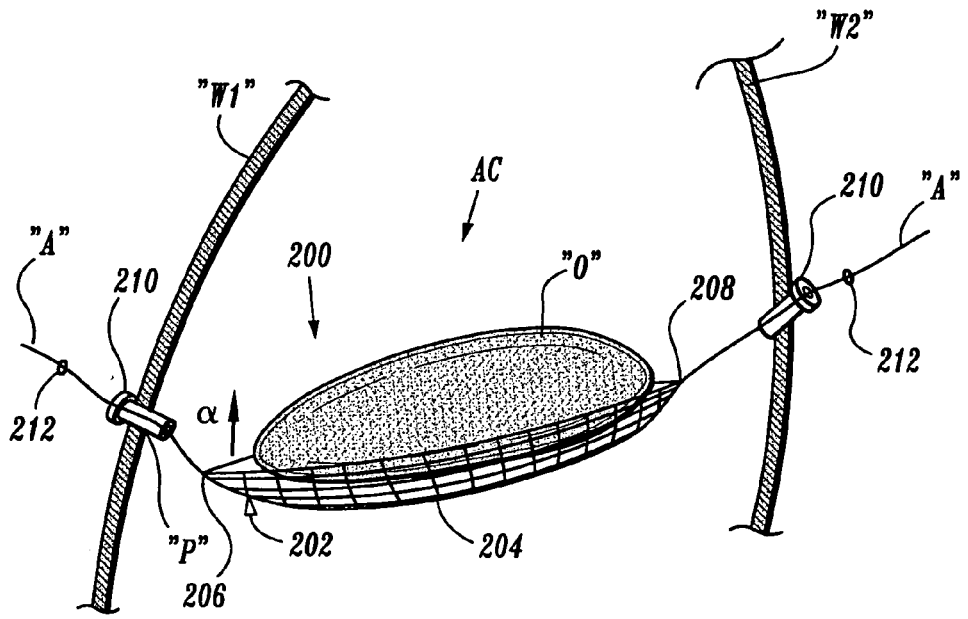
FIG. 11 is a schematic illustration of a method in accordance with the embodiment of FIGS. 8–10, at a later stage in the method.
Figure 12:
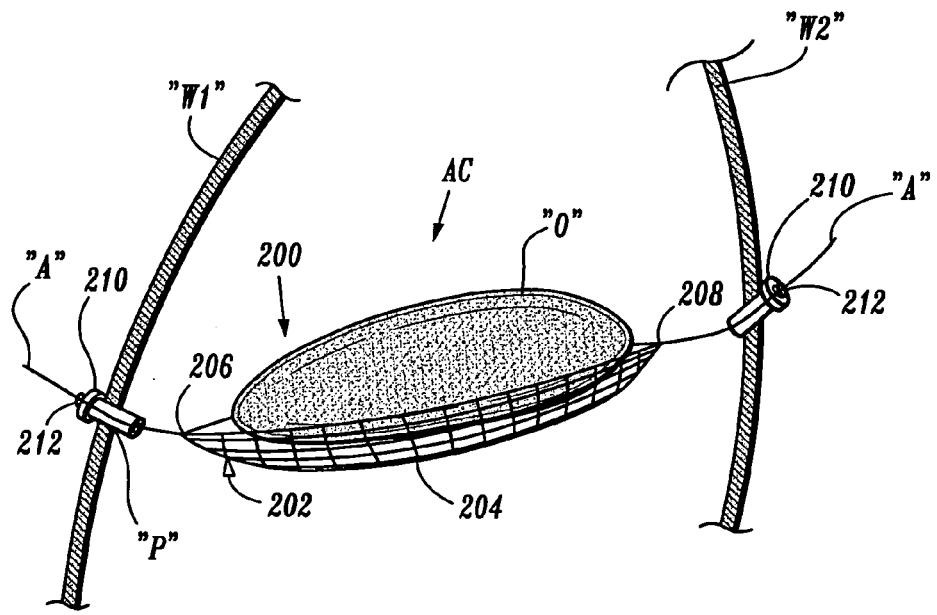
FIG. 12 is a schematic illustration of a method in accordance with the embodiment of FIGS. 8–11, at a later stage in the method.

As seen in FIG. 11, sling section 204 of retractor 202 is then opened and placed over and around body organ "O". With sling section 204 in place, pulling on either end of suture "A", places sling section 204 and suture "A" in tension, thereby retracting body organ "O" in direction "α".

Preferably, as described above, ports 210 are positioned at locations on abdominal walls "W1, W2" such that tensioning of suture "A", which in turn tensions sling section 204, results in the movement and retraction of body organ "O" in direction "α". Similar to retraction system 100 described above, retraction system 200 can further include an anchor 212 coupled to each end of the suture "A" or sutures adjacent the outer surface of abdominal walls "W1, W2". Thus, after the ends of suture "A" have been tensioned, anchors 212 are attached to sutures "A" in order to maintain suture "A" in tension and in order to prevent suture "A" from slipping back into the abdominal cavity. In accordance with the present disclosure, suture "A" provides support to ends 206, 208 of sling 204. An external support may be attached to the suture or sutures in certain embodiments. The sling-type retraction device may be used in the embodiments depicted in FIGS. 1–7C or FIGS. 13–15.

Removal of retractor 202 is accomplished by releasing either or both ends of suture "A" from abdominal walls "W1, W2" to thereby allow body organ "O" to substantially return to its pre-retracted position in abdominal cavity "AC". An end of suture "A" can then be pulled on to thereby withdraw retractor 202 from abdominal cavity "AC".

Figure 13:
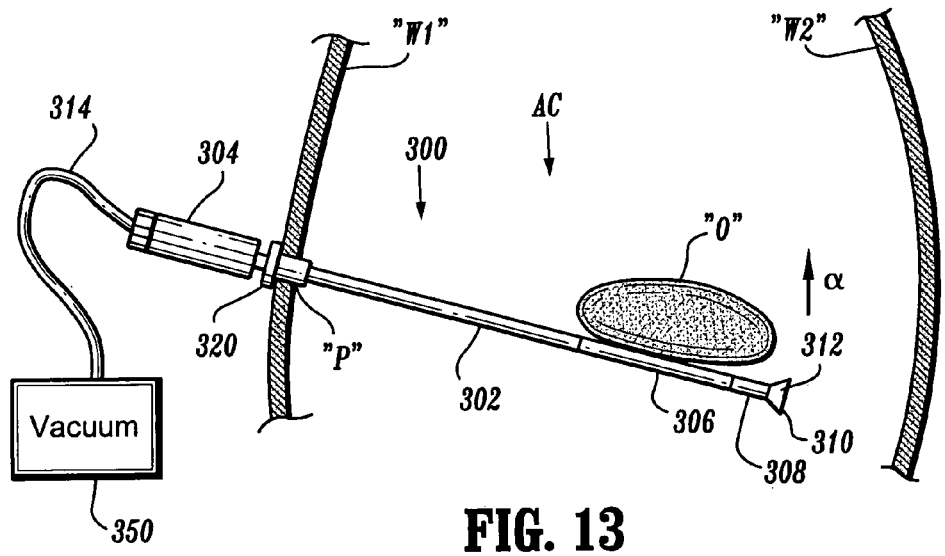
FIG. 13 is a schematic illustration of a method in accordance with yet another embodiment of the present disclosure.
Figure 14:
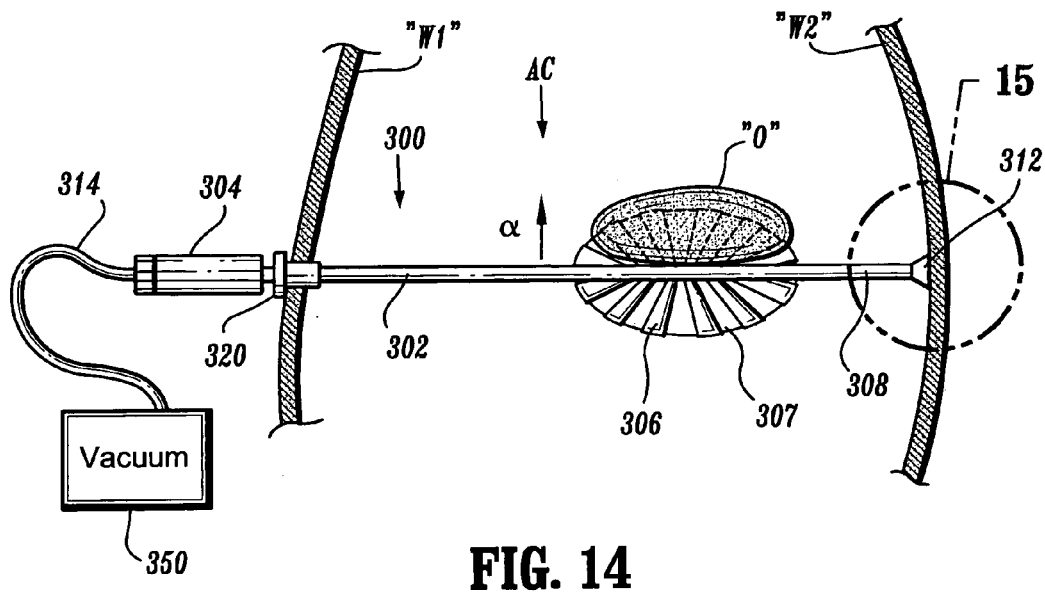
FIG. 14 is a schematic illustration of a method in accordance with the embodiment of FIG. 13, at a later stage in the method.
Figure 15:
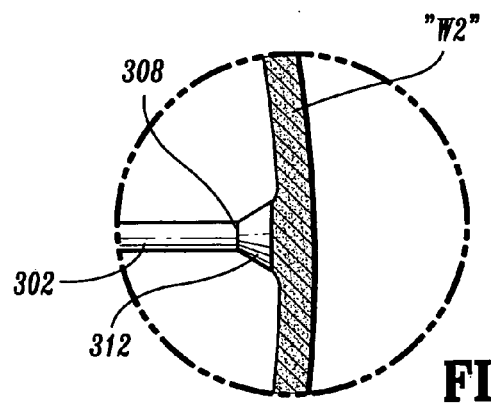
FIG. 15 is an enlarged detail view of the distal end of the retraction system in accordance with the embodiment of FIGS. 13 and 14.

Turning now to FIGS. 13–15, yet another embodiment of a retraction system in accordance with the present disclosure is shown generally as 300. Retraction system 300 includes an elongate shaft 302 extending distally from a handle portion 304. Retraction system 300 further includes a retractor device 306 preferably disposed at a predetermined location along shaft 302, between handle portion 304 and distal end 308 of shaft 302.

Retraction system 300 further includes an anchoring device 310 operatively coupled to distal end 308 of shaft 302. As seen in FIGS. 13–15, anchoring device 310 can be characterized as a suction device 312 which is configured and adapted to be anchored to an inner surface of abdominal wall "W2" via a vacuuming/suctioning effect transmitted thereto. It is contemplated that suction device 312 is fluidly coupled to a vacuum source 350 via a vacuum tube 314 which extends through handle 304 and shaft 302 in order to produce the vacuum/suction effect in suction device 312. Preferably, vacuum tube 314 includes a distal end in fluid communication with suction device 312 and a proximal end in fluid communication with vacuum source 350.

Preferably, retractor device 306, in accordance with the present disclosure, is similar in form and function to the retractor portion disclosed in commonly assigned U.S. Pat. No. 5,456,695 to Herve Dallemange, the disclosure of which is hereby incorporated by reference herein. In particular, it is envisioned that retractor device 306 includes a plurality of cooperating interleaved blade members 307 pivotally mounted within a supporting yoke. Blades members 307 are preferably configured and adapted to move between a first position (i.e., closed) wherein blade members 306 are in longitudinal alignment with shaft 302 and a second position (i.e., open) wherein blade members 306 are disposed in a symmetric fan-like configuration, oriented in a distal and/or proximal direction.

It is envisioned that retraction system 300 preferably further includes at least one port 320, i.e., a trocar cannula, configured and adapted to provide access into abdominal cavity "AC" and through which shaft 302 can pass. Preferably, port 320 creates an air tight seal around shaft 302 and in abdominal wall "W1" to thereby prevent the escape of insufflation gas from abdominal cavity "AC".

With particular reference to FIGS. 13 and 14, a preferred method of using retraction system 300 will now be described. In use, retraction system 300 is configured and adapted to retract body organ "O" in direction "α" in order to provide the surgeon with an enlarged space and increased room to operate. Accordingly, it is preferred that anchoring device 310 (i.e., suction device 312 herein) of retractor system 300 is inserted into the abdominal cavity, through insertion point "P" formed in abdominal wall "W1", at a location which is spaced a longitudinal distance, in direction "α", from the plane defined by body organ "O". Retraction system 300 is then advanced through abdominal cavity "AC", in a direction substantially opposite to direction "α", until anchoring device 310 is advanced past body organ "O" and retraction portion 306 is in close proximity to body organ "O".

Retractor portion 306 is then deployed from the closed position to the open position in order to increase the surface area against which body organ "O" contacts retractor portion 306. Shaft 302 is then rotated, about insertion point "P", such that anchoring device 310 is moved in direction "α". As shaft 302 is rotated to move anchoring device 310 in direction "α", body organ "O" is moved in direction "α". Once body organ "O" is sufficiently moved in direction "α" and sufficiently retracted, retraction system 300 is further advanced through abdominal cavity "AC" until anchoring device 310 is in operable proximity to abdominal wall "W2".

With anchoring device 310 in operable proximity to abdominal wall "W2", anchoring device 310 is activated in order to anchor and secure the distal end of retraction system 300 against the inner surface of abdominal wall "W2". In particular, vacuum source 350 is activated to transmit a vacuum/suctioning effect to suction device 312 thereby drawing the inner surface of abdominal wall "W2" into suction device 312. In accordance with the principles of the present disclosure, anchoring device 310 provides support to distal end 308 of shaft 302. External supports may be used at insertion point "P" and/or suction device 312. Suction device 312 may be used in the embodiments shown in FIGS. 1–12 to anchor a proximal and/or distal end of the retraction system.

While the retraction system, in accordance with the present disclosure, has been described as being used in connection with surgical procedures performed in the abdominal cavity, it is envisioned that the retraction system disclosed herein can be used in various other surgical procedures. It is envisioned that any of the aspects and/or features of retraction systems disclosed and described herein can be combined with one another to effectively provide a retraction system which is supported at both the proximal and distal ends. It will be understood that various modifications may be made to the embodiments of the presently disclosed retraction system. Therefore, the above description should not be construed as limiting, but merely as an exemplification of preferred embodiments. Those skilled in the art will envision other modifications within the scope of the present disclosure.

What is claimed is:

1. A retraction system, comprising:
   a shaft configured and dimensioned to be inserted into a body cavity;
   a retractor device selectively positionable within a lumen of the shaft, the retractor device includes a pair of resilient bands secured to one another at a first end and a second end, and a sheath encasing the pair of resilient bands, the retractor device includes a biased first configuration, wherein the pair of resilient bands each have a substantially linear configuration and wherein the retractor device is positionable within the lumen of the shaft, and at least a second configuration, wherein the pair of resilient bands each have an arcuate profile, for retraction of the body organ, wherein the retractor device automatically assumes a second configuration when withdrawn from the shaft; and
   at least one securement member operatively coupled to the retractor device for securing the retractor device to a wall of the body cavity, wherein the at least one securement member includes a plurality of sutures operatively coupled to each end of opposite ends of the retractor device.

2. The retraction system of claim 1, further comprising: an anchor operatively couplable to each suture, wherein each anchor is configured and adapted to anchor the sutures wit respect to the wall of the body cavity.

3. The retraction system of claim 1, wherein the retractor device is a sling having a pair of opposed ends.

4. A retraction system, comprising:
   a shaft configured and dimensioned to be inserted into a body cavity;
   a retractor device selectively positionable within the shaft, wherein the retractor device is operatively connected to the shaft at a location along a length of the shaft and spaced a distance from a distal end of the shaft, wherein the retractor device has a first configuration in which the retractor device is housed within the shaft and a second configuration in which the retractor device projects outwardly from the shaft; and
   at least one securement member operatively coupled to the retractor device for securing the retractor device to a wall of the body cavity, wherein the at least one securement member is a suction device operatively connected to a distal end of the shaft, the suction device being configured and adapted to transmit a vacuum effect to the wall of the body cavity.

5. The retraction system of claim 4, wherein the retractor device comprises a plurality of blade members movable to a fanned-out position.

6. A method of retracting, the method comprising the steps of:

inserting a retraction system into the body cavity through an insertion point on a first side of the body cavity, the insertion point being located at a position which is spaced a longitudinal distance from a transverse plane defined by a body organ and/or tissue to be retracted, the retraction system including:

a shaft configured and dimensioned to be inserted into a body cavity;

a retractor device selectively positionable within a lumen of the shaft, the retractor device includes a pair of resilient bands secured to one another at a first end and a second end, and a sheath encasing the pair of resilient bands, the retractor device includes a biased first configuration, wherein the pair of resilient bands each have a substantially linear configuration and wherein the retractor device is positionable within the lumen of the shaft, and at least a second configuration, wherein the pair of resilient bands each have an arcuate profile, for retraction of the body organ, wherein the retractor device automatically assumes a second configuration when withdrawn from the shaft; and at least one securement member operatively coupled to the retractor device for securing the retractor device to a wall of the body cavity;

securing the at least one securement member to a wall of the body cavity opposite the first side, the at least one securement member being secured to the wall at a position spaced a longitudinal distance from the transverse plane; and urging the retractor device against the body organ and/or tissue so as to displace the body organ and/or tissue in the longitudinal direction.

* * * * *